United States Patent [19]

Carlson, Sr. et al.

[11] Patent Number: 5,417,964
[45] Date of Patent: May 23, 1995

[54] PROCESS FOR MANUFACTURING AN ANTIPERSPIRANT STICK

[75] Inventors: Jeffrey R. Carlson, Sr., Pembroke; Craig M. Coe, Buzzards Bay; Angel L. Carrillo, Wellesley; David W. Smith, Tyngsboro; Nancy M. Karassik, Concord, all of Mass.

[73] Assignee: The Gillette Company, Boston, Mass.

[21] Appl. No.: 74,079

[22] Filed: Jun. 9, 1993

[51] Int. Cl.$^6$ .................... A61K 7/34; A61K 7/38
[52] U.S. Cl. .................... 424/66; 424/DIG. 5; 424/68
[58] Field of Search .................... 424/65, 66, DIG. 5

[56] References Cited

U.S. PATENT DOCUMENTS

| | | | |
|---|---|---|---|
| 4,049,792 | 9/1977 | Elsnau | 424/66 |
| 4,126,679 | 11/1978 | Davy | 424/66 |
| 4,280,994 | 7/1981 | Turney | 424/68 |
| 4,722,836 | 2/1988 | Geary | 424/68 |
| 4,724,139 | 2/1988 | Palinczar | 424/66 |
| 4,822,603 | 4/1989 | Farris | 424/66 |
| 4,863,721 | 9/1989 | Beck | 424/47 |
| 4,985,238 | 1/1991 | Tanner | 424/66 |
| 5,178,881 | 1/1993 | Mackles et al. | 424/47 |
| 5,250,291 | 10/1993 | Park et al. | 424/47 |

FOREIGN PATENT DOCUMENTS 396137 7/1990 European Pat. Off. .............. 424/66

OTHER PUBLICATIONS

Antiperspirants and Deodorants (ICI Bulletin) Sep. 1982, published by ICI Americas, Inc., pp. 7 and 8.

Primary Examiner—Dale R. Ore
Attorney, Agent, or Firm—Stephan P. Williams

[57] ABSTRACT

The present invention provides a process for making a solid antiperspirant stick comprising a particulate aluminum antiperspirant salt suspended in an anhydrous carrier vehicle, wherein said carrier vehicle comprises a high melting component which melts at 70° C. or higher. This process includes heating the carrier vehicle in a closed mixing vessel to a temperature in excess of 70° C. preferably in excess of 75° C., to melt the high melting component, adding the antiperspirant salt to the carrier vehicle, and cooling the carrier vehicle to form a solid antiperspirant stick. The improvement of the present invention comprises cooling the carrier vehicle below 70° C., preferably to about 65° C. or less, but above the solidification point prior to adding the antiperspirant salt and maintaining the carrier vehicle below 70° C., preferably at about 65° C. or less, during and after the antiperspirant salt addition, thereby substantially preventing agglomeration of the antiperspirant salt into large particles, especially particles in excess of 60 microns.

30 Claims, No Drawings

5,417,964

PROCESS FOR MANUFACTURING AN ANTIPERSPIRANT STICK

BACKGROUND OF THE INVENTION

The present invention relates to a process for manufacturing an antiperspirant stick.

It is generally known that a solid antiperspirant stick may be fabricated by suspending an antiperspirant salt in a liquefied carrier vehicle, pouring the resulting liquid suspension into a stick mold, and cooling to solidify the product. In such a process the carrier vehicle must be heated to a temperature sufficiently high to melt all of its components. Thus, where the carrier vehicle contains only relatively low melting components (m.p. <70° C.), it is not necessary to heat the batch above 70° C. Typical of such systems are those described in U.S. Pat. No. 4,126,679 (Davy) and U.S. Pat. No. 4,722,836 (Geary). Both Davy and Geary melt a carrier vehicle comprising cyclomethicone and stearyl alcohol at about 65° or 66° C., add an ultrafine aluminum chlorohydrate salt, cool the mixture to a few degrees above the solidification point, pour the mixture into stick molds, and cool to solidify the product.

Where the carrier vehicle contains one or more high melting components (m.p. >70° C.), then the batch must be heated above 70° C. in order to melt all the components. Typical of such systems are those described in U.S. Pat. No. 4,049,792 (Elsnau), U.S. Pat. No. 4,724,139 (Palinczar), U.S. Pat. No. 4,822,603 (Farris, U.S. Pat. No. 4,863,721 (Beck) and U.S. Pat. No. 4,985,238 (Tanner), which employ a high melting point wax (for example, castor wax) as one component of the carrier vehicle in addition to a variety of other typical low melting components (for example, volatile silicone, non-volatile silicone, stearyl alcohol, paraffinic hydrocarbons, PPG-14-butyl ether, among others). To manufacture an antiperspirant stick in accordance with the teachings of the above patents, the components of the carrier vehicle are mixed and heated to a temperature above 70° C. sufficient to melt all of the components (typically above 80° C.), the antiperspirant salt is added before the heating step or shortly after all the components are melted (that is, while the carrier vehicle is still hot), the mixture is cooled to a few degrees above the solidification point (typically 50°-55° C.), poured into stick molds, then cooled to solidify the product. A similar process is described in EP 396,137 (Vu), but the temperature is not allowed to exceed 80° C. in order to prevent the polyethylene-vinyl acetate gelling agent from becoming cloudy.

It has now been discovered that when a particulate antiperspirant salt, especially one where 90% of the particles are below 11 microns, is suspended in a substantially anhydrous carrier vehicle which comprises at least one component which melts at 70° C. or higher, and the suspension is heated above 70° C. in a closed mixing vessel, then cooled in the conventional manner, the resulting antiperspirant stick contains a significant amount of agglomerated antiperspirant salt particles, typically over 60 microns in size, and in some cases in excess of 100 microns. The presence of such large particles significantly detracts from the aesthetics of the product, producing a gritty feel. Moreover, if the product contains no or inadequate suspending agents, such large particles will collect at the top or bottom of the container, depending on how it is filled, thus resulting in a non-homogeneous product. The presence of brownish crystalline particles substantially detracts from the appearance of the product as well.

As a result of considerable investigation and experimentation, and without being bound by any theory, it is believed that the afore-described process produces agglomerated antiperspirant salt particles by the following mechanism. When the temperature of the batch (that is, antiperspirant salt and carrier) exceeds 70° C., and especially 80° C., some of the water of hydration normally present in the antiperspirant salt is driven off, condenses on the mixing vessel walls and cover, then falls back into the solution as small droplets due to the agitation. These small droplets attract and agglomerate small antiperspirant salt particles, forming larger particles. Since the water which condenses on the mixing vessel is acidic, it tends to corrode the mixing vessel and carry back minute amounts of metal contaminants with it into the vehicle. These contaminants cause the agglomerated particles to become off-colored, typically brownish in color.

It is an object of the present invention to provide a process for producing a solid antiperspirant stick which contains a high melting component while substantially preventing the agglomeration of the antiperspirant salt into large particles.

SUMMARY OF THE INVENTION

The present invention provides an improvement in the process for making a solid antiperspirant stick comprising a particulate aluminum antiperspirant salt suspended in an anhydrous carrier vehicle, wherein said carrier vehicle comprises a high melting component which melts at 70° C. or higher. The basic process includes heating the carrier vehicle in a closed mixing vessel to a temperature in excess of 70° C., preferably in excess of 75° C., to melt the high melting component, adding the antiperspirant salt to the carrier vehicle, and cooling the carrier vehicle to form a solid antiperspirant stick. The improvement of the present invention comprises cooling the carrier vehicle below 70° C., preferably to about 65° C. or less, but above the solidification point prior to adding the antiperspirant salt and maintaining the carrier vehicle below 70° C., preferably at about 65° C. or less, during and after the antiperspirant salt addition, thereby substantially preventing agglomeration of the antiperspirant salt into large particles, especially particles in excess of 60 microns.

DETAILED DESCRIPTION OF THE INVENTION

In accordance with the present invention, there is provided a process for making a solid antiperspirant stick comprising a particulate aluminum antiperspirant salt suspended in an anhydrous carrier vehicle, wherein said carrier vehicle comprises a low melting component which melts below 65° C. and a high melting component which melts at about 70° C. or higher, which process comprises the following sequential steps:

(a) mixing said high melting component with all or a portion of said low melting component in a closed mixing vessel at a temperature in excess of 70° C. to melt said high melting component and form a substantially homogenous solution;

(b) cooling said solution to a temperature below 70° C. but above the solidification point of said solution;

(c) adding any remaining portion of said low melting component not added in step (a) and said antiperspirant salt to said cooled solution in a closed mixing vessel to form a suspension of said antiperspirant salt in said cooled solution;

(d) cooling said solution to a temperature of about 1° to 10° C. above the solidification point; and (e) pouring said solution into stick form molds and cooling to form a solid antiperspirant stick.

In carrying out the aforedescribed process, it is generally preferred that step (a) is performed at a temperature of about 75° C. or higher, most preferably at about 80° C. or higher, in order to melt all of the components of the carrier vehicle more quickly. It is also preferred to cool the solution in step (b) to about 65° C. or less in order to minimize the possibility of water vapor formation and condensation. It should also be noted that while no additional cooling may be necessary in step (d) if the temperature attained in step (b) is sufficiently low (i.e., within 1° to 10° C. above the solidification point), it is preferred to cool the solution in step (d) to within a few degrees, most preferably 1° to 4° C., above the solidification point. It is also preferred to pass a dry gas such as nitrogen or air ($<11\%$ relative humidity) through the head space of the closed mixing vessel during the process, especially step (c), in order to purge or sweep out any moisture that might arise in spite of the aforementioned precautions, such as might occur when wetter antiperspirant salts are employed. By following the above process steps, one will obtain a solid antiperspirant stick which is substantially free of agglomerated antiperspirant salt particles in excess of 100 microns, more preferably 80 microns, and most preferably 60 microns.

The components which may be utilized to make solid antiperspirant sticks in accordance with the process of the present invention may be any of those which are conventionally known for use in formulating antiperspirant sticks. Naturally, of course, the formulation should contain at least one high melting component which melts at 70° C. or higher since, otherwise, there would be no reason to heat the composition above that temperature and, thus, realize the advantages attained with this invention.

The particulate aluminum antiperspirant salt which is utilized may be any of the conventional aluminum and aluminum-zirconium antiperspirant salts known to be useful in antiperspirant sticks. These salts typically comprise about 5 to 40%, preferably 15 to 30% by weight, of the antiperspirant stick, may be impalpable or microspherical in form, and preferably have particle sizes in the range of about 1 to about 50 microns, most preferably at least 90% of the particles being under 11 microns. Such salts typically include the aluminum halides and aluminum hydroxy halides (e.g., aluminum chlorohydrate) and mixtures or complexes thereof with zirconyl oxyhalides and zirconyl hydroxyhalides (e.g. aluminum-zirconium chlorohydrate).

Typical aluminum salts are those having the general formula $Al_2(OH)_{6-a}X_a \cdot nH_2O$ wherein X is Cl, Br, I or $NO_3$, a is about 0.3 to about 4, preferably about 1 to 2, such that the Al to X mole ratio is about 1/1 to 2.1/1, and n is 1 to 6, preferably about 2. Most preferably, the aluminum salt is aluminum chlorohydrate (i.e., X is Cl) and a is about 1, such that the aluminum to chlorine mole ratio is about 1.9/1 to 2.1/1.

The aluminum-zirconium salts are typically complexes or mixtures of the above aluminum salts with zirconium salts of the formula $ZrO(OH)_{2-pb}Y_b \cdot mH_2O$ wherein Y is Cl, Br, I, $NO_3$ or $SO_4$, b is about 0.9 to 2, p is the valence of Y, and m is about 1 to 7. Preferably the zirconium salt is zirconyl hydroxychloride of the formula $ZrO(OH)_{2-b}Cl_b \cdot mH_2O$ wherein b is about 1 to 2, preferably about 1.5 to about 1.87. It is also preferred that the aluminum-zirconium complex has an Al:Zr ratio of about 1.67 to about 12.5, most preferably about 2.5 to 5, and a Metal:Cl ratio of about 0.73 to about 1.93. Such complexes also typically contain a neutral amino acid, preferably glycine.

It is especially preferred to use high efficacy forms of aluminum and aluminum-zirconium salts such as those described, for example, in GB 2,048,229, U.S. Pat. No. 4,359,456, EP 183,171, EP 337,464, EP 366,230, EP 405,598, U.S. Pat. No. 4,775,528, and U.S. Pat. No. 4,871,525. Such salts, when reconstituted as 10% aqueous solutions, typically produce an HPLC chromatogram wherein at least 80% of the aluminum is contained in two successive peaks, conveniently labelled peaks 3 and 4, wherein the ratio of the area under peak 4 to the area under peak 3 is at least 0.70, preferably at least 1.0 or higher.

The afore-described antiperspirant salt is suspended in an anhydrous carrier vehicle which comprises about 60 to 95%, preferably about 70 to 85%, of the antiperspirant stick. The anhydrous carrier vehicle comprises at least one high melting component which melts at 70° C. or higher. Typically the carrier vehicle comprises one or more high melting components which melt at temperatures of about 70° C. or higher, and one or more low melting components which melt at temperatures below 65° C.

The high melting components may include any materials suitable for use in antiperspirant sticks and which melt at temperatures of about 70° C. or higher. Typical of such materials are the high melting point waxes. These include beeswax, spermaceti, carnauba, bayberry, candelilla, montan, ozokerite, ceresin, and paraffin waxes, synthetic waxes such as Fisher-Tropsch waxes, semimicrocrystalline and microcrystalline waxes, hydrogenated jojoba oil, and hydrogenated castor oil (castor wax). The preferred wax is hydrogenated castor oil. Other suitable high melting components include various types of high melting gelling agents such as polyethylene-vinylacetate copolymers, polyethylene homopolymers, and substituted and unsubstituted dibenzylidene alditols. Typically, the high melting components comprise about 1 to 25%, preferably about 2 to 15%, of the antiperspirant stick.

The carrier also typically includes one or more low melting components which melt at temperatures of about 65° C. or less. These include, for example, volatile silicones, non-volatile silicones, $C_{3-6}$ diols, fatty alcohols, fatty alcohol esters, fatty acid esters, fatty amides, non-volatile paraffinic hydrocarbons, polyethlene glycols, polypropylene glycols, polyethylene and/or polypropylene glycol ethers of $C_{4-20}$ alcohols, polyethylene and/or polypropylene glycol esters of fatty acids, and mixtures thereof. The term "fatty" is intended to include hydrocarbon chains of about 8 to 30 carbon atoms, preferably about 12 to 18 carbon atoms. An especially preferred combination of low melting components comprises a volatile silicone, a low melting point wax, and a non-volatile emollient.

Volatile silicones include the cyclic polydimethylsiloxanes, also known as cyclomethicones, which have from about 3 to about 7 silicon atoms, and the linear polydimethylsiloxanes, also known as dimethicones, which have from about 2 to about 9 silicon atoms. The linear volatile silicones generally have viscosities of less than about 5 centistokes at 25° C. while the cyclic volatile silicones have viscosities under 10 centistokes. "Volatile" means that the material has a measurable vapor pressure at room temperature. Preferred are the cyclomethicones such as DC 344 and DC 345, available from Dow Corning Corporation.

Non-volatile silicones include polyalkylsiloxanes, polyalkylaryl siloxanes, and polyethersiloxane copolymers with viscosities of about 5 to about 100,000 centistokes at 25° C. These include polydimethylsiloxanes with viscosities of about 10 to about 400 centistokes at 25° C. (e.g. DC 200), polymethylphenylsiloxanes with viscosities of about 15 to about 65 centistokes, and polyoxyalkyleneether dimethyl siloxane copolymers with viscosities of about 1200 to about 1500 centistokes.

Useful $C_{3-6}$ diols include propylene glycol, butylene glycol, dipropylene glycol and hexylene glycol. Fatty alcohols include stearyl alcohol, cetyl alcohol, myristyl alcohol, oleyl alcohol, and lauryl alcohol. Fatty alcohol esters include $C_{12-15}$ alcohols benzoate, myristyl lactate, cetyl acetate, and myristyl octanoate. Fatty acid esters include isopropyl palmitate, myristyl myristate, and glyceryl monostearate. Fatty amides include stearamide, stearamide MEA, stearamide MEA-stearate, lauramide DEA, and myristamide MIPA.

Non-volatile paraffinic hydrocarbons include mineral oils and branched chain hydrocarbons with about 16 to 68, preferably about 20 to 40, carbon atoms. A preferred material is hydrogenated polyisobutene with about 24 carbon atoms. Suitable polyethylene glycols and polypropylene glycols will typically have molecular weights of about 500 to 6000, such as PEG-10, PEG-40, PEG-150 and PPG-20. Polyethylene and/or polypropylene glycol ethers of $C_{4-20}$ alcohols include PPG-10 Butanediol, PPG-14 Butyl Ether, PPG-5-Buteth-7, PPG-3-Isosteareth-9, PPG-3-Myreth-3, Oleth-10, and Steareth-20. Polyethylene and/or polypropylene glycol esters of fatty acids include PEG-8 Distearate, PEG-10 Dioleate, and PPG-26 Oleate.

The above list of materials is by way of example only and is not intended to be a comprehensive list of all potential antiperspirant stick components. Numerous other low melting waxes, non-volatile emollients and other suitable components are readily identifiable to those skilled in the art. Of course, other conventional stick ingredients such as colloidal silicas, particulate polyolefins, talcum materials, fragrances, dyes and preservatives may also be included as desired.

A most preferred antiperspirant stick formulation will comprise about 15 to 30% antiperspirant salt, preferably aluminum-zirconium chlorohydrate particles at least 90% of which are below about 11 microns, about 40 to 50% cyclomethicone, about 13 to 18% stearyl alcohol, about 4–6% PPG-10 butanediol, about 3 to 5% $C_{12-15}$ alcohols benzoate and about 2 to 4% hydrogenated castor oil.

EXAMPLE

Two commercial size batches of an antiperspirant composition, with each batch weighing approximately 4500 kg, were made with the following components:

| Component | % by weight |
|---|---|
| Cyclomethicone (DC345) | 44.6 |
| Aluminum-zirconium-tetrachlorohydrex-Gly | 22.7 |
| (90% < 11 microns) | |
| Stearyl alcohol | 15.6 |
| PPG-10 Butanediol | 4.8 |
| $C_{12-15}$ Alcohols Benzoate | 3.8 |
| Hydrogenated castor oil | 2.8 |
| Myristyl myristate | 1.9 |
| PEG-8 Distearate | 0.9 |
| Fragrance | 2.9 |

A first batch was made according to the conventional procedure. A portion of the cyclomethicone (approximately 90–95%) was charged to a closed, stirred pre-mix tank under nitrogen sweep, to which was added the $C_{12-15}$ Alcohols benzoate and the antiperspirant salt at room temperature. This pre-mix was filtered through a 40 mesh filter, charged to a closed, stirred mixing tank under nitrogen sweep, and heated to about 85° C. The remaining components, except for the fragrance, were added and the mixture maintained at about 85° C. until all components were melted to form a homogeneous solution (about 45 minutes). This solution was cooled to about 64° C., when the fragrance was added, then further cooled to about 52° to 56° C. It was then poured into stick molds and allowed to solidify. The resulting antiperspirant sticks were found to be unacceptable since they contained a substantial number of brownish agglomerated salt particles greater than 100 microns in size.

A second batch was made according to the procedure of this invention. A portion of the cyclomethicone (approximately 90–95%) was charged to a closed, stirred pre-mix tank under nitrogen sweep, to which was added the PPG-10 Butanediol, the $C_{12-15}$ Alcohols benzoate and the antiperspirant salt at room temperature. This pre-mix was filtered through a 40 mesh filter and warmed to about 65° C. The remaining ingredients, except for the fragrance, were charged to a closed, stirred mixing tank under nitrogen sweep and heated to about 85° C. until all components were melted to form a homogeneous solution (about 45 minutes). After cooling this solution to about 65° C., the pre-mix and fragrance were added. This solution was further cooled to about 52° C. to 57° C., poured into stick molds and allowed to solidify. The resulting antiperspirant sticks had excellent aesthetic properties and were found to be substantially free of agglomerated salt particles greater than 60 microns.

What is claimed is:

1. In a process for making a solid antiperspirant stick comprising a particulate aluminum antiperspirant salt suspended in an anhydrous carrier vehicle, wherein said carrier vehicle comprises a high melting component which melts at 70° C. or higher, said process comprising heating said carrier vehicle in a closed mixing vessel to a temperature in excess of 70° C. to melt said high melting component, adding said antiperspirant salt to said carrier vehicle, and cooling said carrier vehicle to form a solid antiperspirant stick, the improvement comprising cooling said carrier vehicle below 70° C. but above the solidification point prior to adding said antiperspirant salt and maintaining said carrier vehicle below 70° C. during and after said antiperspirant salt addition, thereby substantially preventing agglomeration of said antiperspirant salt into large particles.

2. The process of claim 1 wherein said carrier vehicle is heated to a temperature of 75° C. or higher to melt said high melting component, then is cooled to a temperature of about 65° C. or less prior to adding said antiperspirant salt.

3. The process of claim 2 wherein said high melting component comprises a high melting point wax.

4. The process of claim 3 wherein said antiperspirant salt comprises particles at least 90% of which are below about 11 microns.

5. The process of claim 4 wherein said high melting point wax comprises hydrogenated castor oil.

6. The process of claim 2 wherein said carrier vehicle comprises volatile silicone in addition to said high melting component.

7. The process of claim 6 wherein said high melting component comprises a high melting point wax.

8. The process of claim 7 wherein said antiperspirant salt comprises particles at least 90% of which are below about 11 microns.

9. The process of claim 8 wherein said high melting point wax comprises hydrogenated castor oil.

10. The process of claim 2 wherein said carrier vehicle is heated to a temperature of 80° C. or higher to melt said high melting component.

11. The process of claim 10 wherein said carrier vehicle comprises, in addition to said high melting component, one or more components selected from the group consisting of volatile silicones, non-volatile silicones, $C_{3-6}$ diols, fatty alcohols, fatty alcohol esters, fatty acid esters, fatty amides, non-volatile paraffinic hydrocarbons, polyethylene glycols, polypropylene glycols, polyethylene and/or polypropylene glycol ethers of $C_{4-20}$ alcohols, polyethylene and/or polypropylene glycol esters of fatty acids, and mixtures thereof.

12. The process of claim 11 wherein said carrier vehicle comprises, in addition to said high melting component, one or more components selected from the group consisting of cyclomethicone, dimethicone, propylene glycol, stearyl alcohol, $C_{12-15}$ alcohols benzoate, myristyl myristate, isopropyl myristate, PPG-10 butanediol, hydrogenated polyisobutene, PEG-8 distearate, and mixtures thereof.

13. The process of claim 12 wherein said antiperspirant salt comprises particles at least 90% of which are below about 11 microns.

14. The process of claim 13 wherein said antiperspirant salt is aluminum-zirconium chlorohydrate.

15. The process of claim 14 wherein said high melting component comprises hydrogenated castor oil.

16. A process of making a solid antiperspirant stick comprising a particulate aluminum antiperspirant salt suspended in an anhydrous carrier vehicle, wherein said carrier vehicle comprises a low melting component which melts below 65° C. and a high melting component which melts at about 70° C. or higher, which process comprises the following sequential steps:

(a) mixing said high melting component with all or a portion of said low melting component in a closed mixing vessel at a temperature in excess of 70° C. to melt said high melting component and form a substantially homogenous solution;

(b) cooling said solution to a temperature below 70° C. but above the solidification point of said solution;

(c) adding any remaining portion of said low melting component not added in step (a) and said antiperspirant salt to said cooled solution in a closed mixing vessel to form a suspension of said antiperspirant salt in said cooled solution;

(d) cooling said solution to a temperature of about 1° to 10° C. above the solidification point; and (e) pouring said solution into stick form molds and cooling to form a solid antiperspirant stick.

17. The process of claim 16 wherein the mixing of step (a) is performed at a temperature of about 80° C. or higher.

18. The process of claim 17 wherein said solution is cooled in step (b) to a temperature of about 65° C. or less.

19. The process of claim 18 wherein said low melting component comprises one or more components selected from the group consisting of volatile silicones, non-volatile silicones, $C_{3-6}$ diols, fatty alcohols, fatty alcohol esters, fatty acid esters, fatty amides, non-volatile paraffinic hydrocarbons, polyethylene glycols, polypropylene glycols, polyethylene and/or polypropylene glycol ethers of $C_{4-20}$ alcohols, polyethylene and/or polypropylene glycol esters of fatty acids, and mixtures thereof.

20. The process of claim 19 wherein said high melting component comprises a high melting point wax.

21. The process of claim 20 wherein said low melting component comprises one or more components selected from the group consisting of cyclomethicone, dimethicone, propylene glycol, stearyl alcohol, $C_{12-15}$ alcohols benzoate, myristyl myristate, isopropyl myristate, PPG-10 butanediol, hydrogenated polyisobutene, PEG-8 distearate, and mixtures thereof.

22. The process of claim 21 wherein said high melting component comprises hydrogenated castor oil.

23. The process of claim 22 wherein said antiperspirant salt comprises aluminum-zirconium chlorohydrate particles at least 90% of which are below about 11 microns.

24. The process of claim 23 wherein step(c) is conducted under a dry gas purge.

25. The process of claim 24 wherein said antiperspirant stick comprises about 15 to 30% antiperspirant salt, about 40 to 50% cyclomethicone, about 13 to 18% stearyl alcohol, about 4–6% PPG-10 butanediol, about 3 to 5% $C_{12-15}$ alcohols benzoate and about 2–4% hydrogenated castor oil.

26. The process of claim 25 wherein said stearyl alcohol, said hydrogenated castor oil and a small portion of said cyclomethicone are mixed in step(a), and said antiperspirant salt, said PPG-10 butanediol, said $C_{12-15}$ alcohols benzoate, and the balance of said cylcomethicone are combined as a pre-mix and heated to about 65° C. under a dry gas purge prior to addition in step(c).

27. The process of claim 18 wherein said low melting component comprises a volatile silicone, a low melting point wax, and a non-volatile emollient, said high melting component comprises a high melting point wax, and said antiperspirant salt comprises aluminum-zirconium chlorohydrate particles at least 90% of which are below about 11 microns.

28. An antiperspirant stick made in accordance with the process of claim 16, substantially free of agglomerated antiperspirant salt particles in excess of 60 microns.

29. An antiperspirant stick made in accordance with the process of claim 20.

30. An antiperspirant stick made in accordance with the process of claim 25.

* * * * *